(12) United States Patent
Veis et al.

(10) Patent No.: US 10,363,161 B2
(45) Date of Patent: Jul. 30, 2019

(54) SLEEP APNEA ORAL APPLIANCE FOR USE DURING ORTHODONTIC TREATMENT

(71) Applicants: Robin Veis, Chatsworth, CA (US); Payam Ataii, Laguna, CA (US)

(72) Inventors: Robin Veis, Chatsworth, CA (US); Payam Ataii, Laguna, CA (US)

(73) Assignee: SELANE PRODUCTS, INC., Chatsworth, CA (US)

( * ) Notice: Subject to any disclaimer, the term of this patent is extended or adjusted under 35 U.S.C. 154(b) by 0 days.

(21) Appl. No.: 15/954,500

(22) Filed: Apr. 16, 2018

(65) Prior Publication Data

US 2018/0263807 A1    Sep. 20, 2018

Related U.S. Application Data

(63) Continuation of application No. 15/323,715, filed as application No. PCT/US2015/039147 on Jul. 2, 2015, now Pat. No. 9,949,867.

(60) Provisional application No. 62/020,384, filed on Jul. 2, 2014.

(51) Int. Cl.
- *A61C 5/00* (2017.01)
- *A61F 5/56* (2006.01)
- *A61C 7/08* (2006.01)
- *A61C 7/10* (2006.01)

(52) U.S. Cl.
CPC ............... *A61F 5/566* (2013.01); *A61C 7/08* (2013.01); *A61C 7/10* (2013.01)

(58) Field of Classification Search
CPC .. A61F 5/566; A61C 7/08; A61C 7/10; A61C 7/36
See application file for complete search history.

(56) References Cited

U.S. PATENT DOCUMENTS

| | | | | |
|---|---|---|---|---|
| 4,755,139 A * | 7/1988 | Abbatte | ............ | A61C 7/08 433/6 |
| 5,683,244 A * | 11/1997 | Truax | ............ | A61C 7/00 433/24 |
| 8,215,312 B2 * | 7/2012 | Garabadian | ............ | A61F 5/566 128/846 |
| 8,517,029 B2 * | 8/2013 | Nelissen | ............ | A61F 5/566 128/848 |
| 8,783,261 B2 * | 7/2014 | Thornton | ............ | A61F 5/566 128/848 |
| 8,839,793 B2 * | 9/2014 | Diaz | ............ | A61F 5/566 128/848 |
| 2005/0028826 A1 | 2/2005 | Palmisano | | |

(Continued)

FOREIGN PATENT DOCUMENTS

| EP | 1312319 A2 | 5/2003 |
|---|---|---|
| WO | 96/29964 A1 | 10/1996 |
| WO | 2010/087824 A1 | 8/2010 |

OTHER PUBLICATIONS

Supplementary European Search Report, corresponding European Patent Application No. 15814943.5, dated Feb. 7, 2018; 8 pages.

*Primary Examiner* — Nicholas D Lucchesi
(74) *Attorney, Agent, or Firm* — Michael F. Fedrick; Loza & Loza, LLP

(57) ABSTRACT

A sleep apnea oral appliance in which a pair of appliance trays are worn over respective orthodontic trays. The appliance trays are adjustable in order to allow them to be used with a series of orthodontic trays.

12 Claims, 9 Drawing Sheets

(56) References Cited

U.S. PATENT DOCUMENTS

| | | | |
|---|---|---|---|
| 2007/0264605 A1* | 11/2007 | Belfor | A61C 7/00 |
| | | | 433/6 |
| 2009/0036889 A1* | 2/2009 | Callender | A61F 5/566 |
| | | | 606/55 |
| 2012/0227750 A1* | 9/2012 | Tucker | A61F 5/566 |
| | | | 128/848 |
| 2013/0089828 A1* | 4/2013 | Borovinskih | A61C 7/08 |
| | | | 433/6 |
| 2014/0072927 A1 | 3/2014 | Diaz | |
| 2015/0079531 A1* | 3/2015 | Heine | A61C 7/36 |
| | | | 433/19 |
| 2015/0245887 A1* | 9/2015 | Izugami | A61C 7/08 |
| | | | 433/6 |
| 2016/0228286 A1* | 8/2016 | Rayek | A61F 5/566 |

* cited by examiner

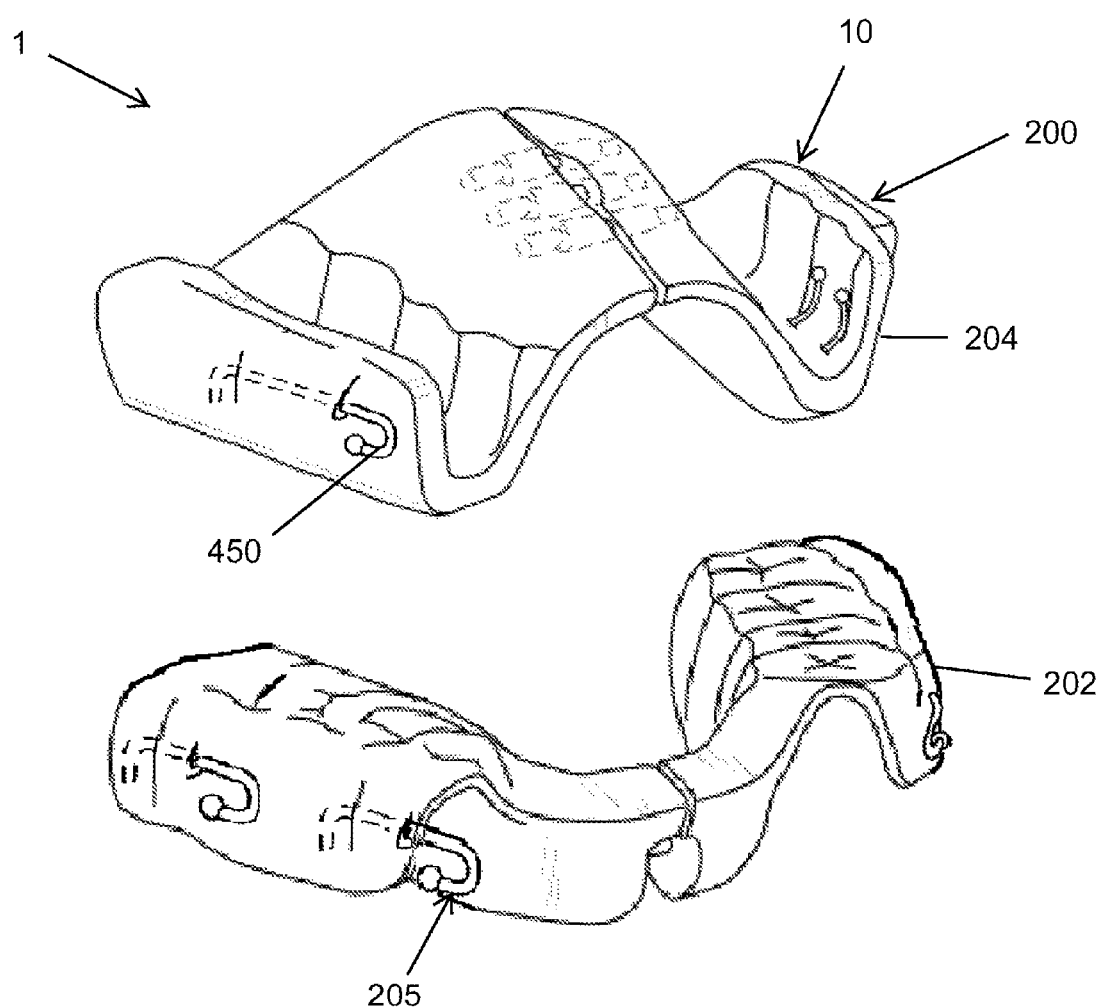

SLEEP APNEA ORAL APPLIANCE FOR USE DURING ORTHODONTIC TREATMENT

CROSS-REFERENCE TO RELATED APPLICATIONS

This application is a continuation of and claims the benefit of priority under 35 U.S.C. § 120 from U.S. patent application Ser. No. 15/323,715, filed on Jan. 3, 2017 and entitled SLEEP APNEA ORAL APPLIANCE FOR USE DURING ORTHODONTIC TREATMENT, which is the U.S. national stage of International Patent Application No. PCT/US2015/039147, filed on Jul. 2, 2015, which claims the benefit of priority under 35 U.S.C. § 120 from U.S. Patent Application No. 62/020,384, filed on Jul. 2, 2014. The disclosures of the foregoing applications are incorporated herein by reference in their entirety.

BACKGROUND

Sleep apnea is a disorder characterized by abnormal pauses in breathing or instances of abnormally low breathing during sleep. Each pause in breathing, called an apnea, can last from a few seconds to minutes (typically lasting 20 to 40 seconds) and may occur 5 to 30 times or more an hour. Sleep apnea results from a partial-to-complete blockage of a subject's airway. Increased air speed through the airway causes an increase in dynamic pressure and a corresponding drop in static pressure. The decreased static pressure can in some instances draw back the lower jaw and tongue and thereby block the airway. This blockage can increase to the point of becoming complete, which at least temporarily interrupts breathing.

There are a variety of factors that contribute to sleep apnea. One factor is the presence of a narrow maxilla and/or mandible in a patient. Maxillary constriction may increase nasal resistance and alter the tongue posture, leading to narrowing of the retroglossal airway. Constriction of the maxilla and/or the mandible generally reduces intraoral air volume and tends to force the tongue back into the posterior airway space, leading to obstructive sleep apnea during sleep.

Orthodontics is a field of dentistry which focuses on the repositioning of a patient's teeth and jaws for aesthetic or other reasons, for example due to the "overcrowding" of a patient's teeth. Orthodontic methods may result in the expansion of a patient's jaw, which provides more room for overcrowded teeth, for example. For patients suffering from sleep apnea, such expansion of the jaw can alleviate sleep apnea, which is exacerbated by maxillary constriction.

Orthodontic methods typically require a subject to make continuous use of an orthodontic appliance for a period of time in order to achieve results. The appliance might consist of "braces," comprising a variety of appliances such as brackets, archwires, and rubber bands, or alternatively may consist of plastic trays worn over a subject's teeth. The use of such appliances precludes the concurrent use of currently available oral appliances for treating sleep apnea. There remains a need therefore for improved devices and methods for treating sleep apnea in users of orthodontic appliances who experience sleep apnea.

SUMMARY

The present invention is an oral appliance that can be used to treat snoring and/or sleep apnea in a subject wearing an orthodontic tray. The oral appliance is comprised of two trays, a first appliance tray and second appliance tray, each adapted to be worn over either the maxillary or mandibular dentition of a subject. For example, the first tray can be an upper tray for receiving an orthodontic tray placed on a subject's maxillary dentition while the second tray can be a lower tray for receiving an orthodontic tray placed on the subject's mandibular dentition.

The first appliance tray and the second appliance tray each have an anterior portion, a posterior portion, a right side, a left side, a buccal side, a lingual side, an inner surface, and an outer surface. These trays each also comprise the following components:
   (i) a right side portion comprising:
      a receptacle bounded by the inner surface of the right side portion and formed to retain a right side of an orthodontic tray;
      one or more clasps extending outwardly from the inner surface of the right side portion;
      at least one projection extending laterally from the buccal side of the right side portion, the projection forming an anchor;
   (ii) a left side portion comprising:
      a receptacle bounded by the inner surface of the left side portion and formed to retain a left side of an orthodontic tray;
      one or more clasps extending outwardly from the inner surface of the left side portion;
      at least one projection extending laterally from the buccal side of the left side portion, the projection forming an anchor; and
   (iii) an expandable lateral connector, such as an expansion screw, for mechanically connecting the left side of the right side portion and the right side of the left side portion of the appliance tray, wherein the expandable lateral connector can be adjusted to lengthen the lateral distance between the right side portion and the left side portion of the first appliance tray.

The two appliance trays are mechanically connected in order to maintain the first appliance tray in a predetermined position with respect to the second appliance tray. In particular, the anchor of the left side portion of the first appliance tray is mechanically connected to the anchor of the left side portion of the second appliance tray, and the anchor of the right side portion of the first appliance tray is mechanically connected to the anchor of the right side portion of the second appliance tray. The anchors can be, for example, a button, a hook, or a Herbst screw, and can be mechanically connected by appropriate connectors, such as orthodontic rubber bands, telescoping shims, and/or plastic connectors.

In one embodiment, the anchor of the first appliance tray has a rearwardly-facing surface and the anchor of the second appliance tray has a forwardly-facing surface. In this embodiment, the rearwardly-facing surface of the first appliance tray engages the forwardly-facing surface of the second appliance tray in order to maintain the relative positions of the first and second appliance trays. In this case, the anchor of the second appliance tray can comprises a flange having an anterior side and a posterior side, where the anterior side comprises the forwardly-facing surface. The posterior side is attached to the second appliance tray by an expandable connector, and the expandable connector can be adjusted to lengthen the lateral distance between the right side portion and the left side portion.

The clasps are selected to be able to engage and grip a tooth surface of a subject, in order to retain the oral appliance. Such clasps can be, for example, Adam's clasps (double clasps), ball clasps, C clasps (three-quarter clasps), Jackson's clasps (full clasps), Southend clasps, Duyzing clasps, Schwarz clasps, Eyelet clasps, or other clasps known to those of skill in the art. Preferably, the receptacles of the first appliance tray and/or the second appliance tray do not extend over the subject's incisors, in order to provide an anterior opening for air flow when the oral appliance is worn by a subject.

The oral appliance is designed to be used together with orthodontic trays, which are used to adjust the tooth position and/or jaw shape of a subject. Such orthodontic trays generally comprise a first orthodontic tray and a second orthodontic tray (e.g., an upper tray and lower tray), and each of these trays includes an anterior portion, a posterior portion, a right side, a left side, an inner surface, and an outer surface. The orthodontic trays used with the present oral appliance are preferably modified to include one or more openings between the outer surface and the inner surface of the orthodontic appliance, corresponding to the positions of the clasps on the first appliance tray, in order to allow at least a portion of each of the clasps to extend through the orthodontic trays and contact a tooth surface of the subject when the orthodontic trays and appliance trays are worn by a subject. Typically, the orthodontic trays comprise a series of first orthodontic trays and a series of second orthodontic trays, where each of the orthodontic trays in the series comprises a different configuration in order to change the position of subject's teeth and/or the shape of the subject's jaw. The receptacles of the appliance trays are preferably configured to receive and retain all of the appliance trays, such that the receptacles of the first appliance tray are shaped to receive all of the first orthodontic trays, and the receptacles of the second appliance tray are shaped to receive all of the second orthodontic trays.

FIGURES

FIG. 9 is a perspective view of another embodiment of the present appliance trays.

DESCRIPTION

Definitions

Figure 1:
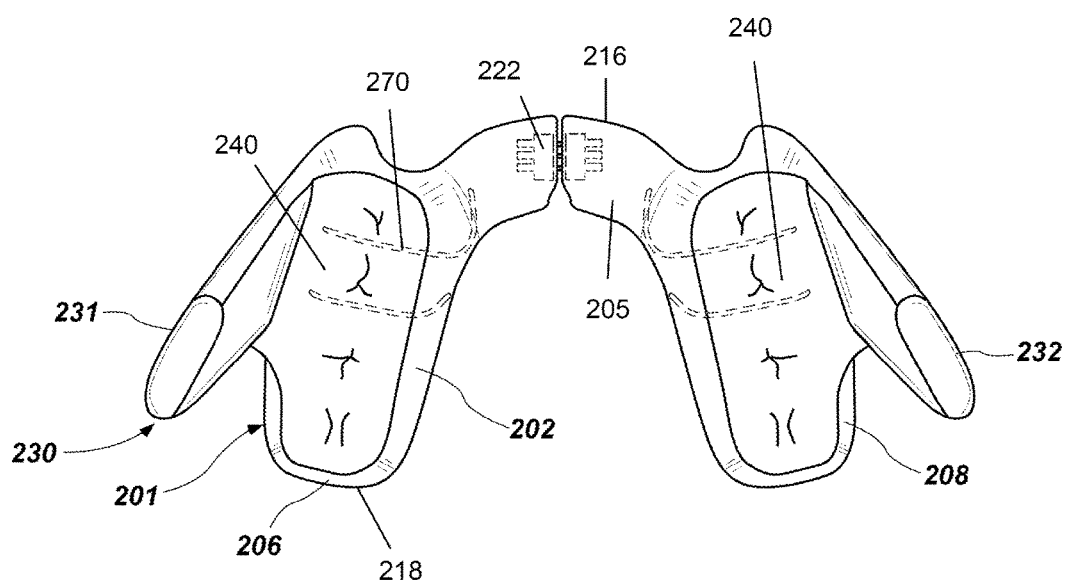
FIG. 1 is a top plan view of a lower appliance tray in one embodiment.
Figure 2:
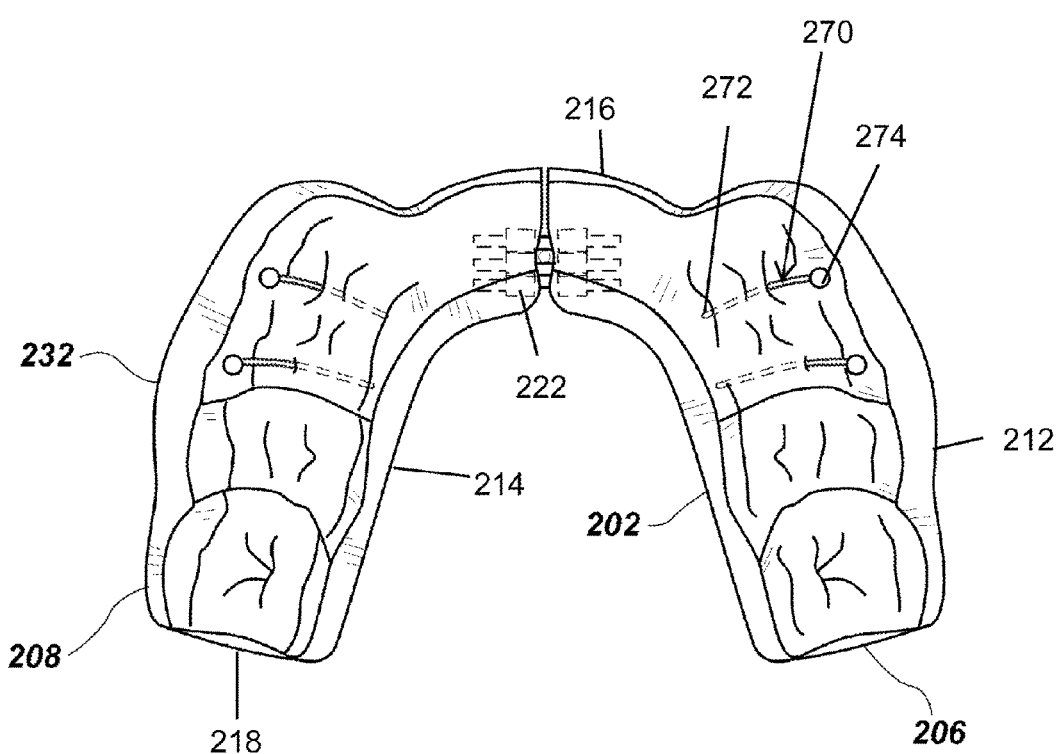
FIG. 2 is bottom plan view of the lower appliance tray of FIG. 1.
Figure 3:
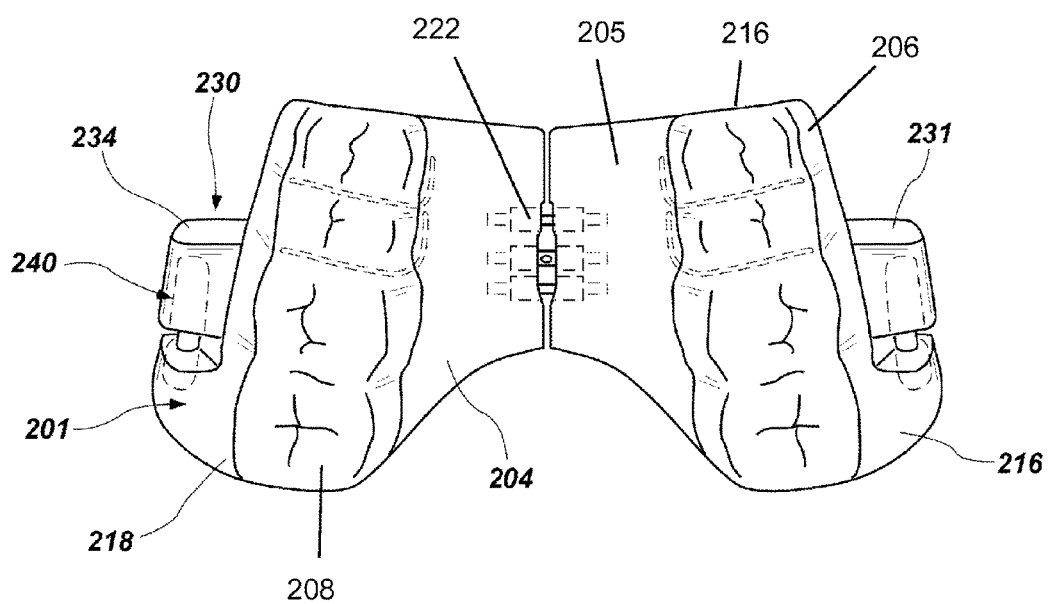
FIG. 3 is a bottom plan view of an upper appliance tray for use with the lower appliance tray of FIG. 1.
Figure 4:
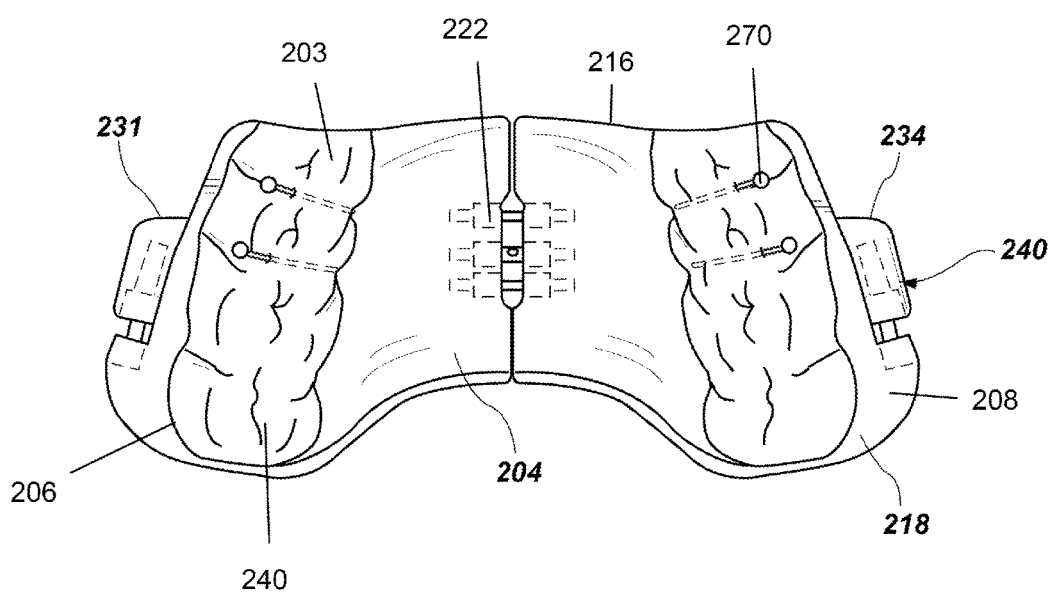
FIG. 4 is top plan view of the upper appliance tray of FIG. 3.
Figure 5:
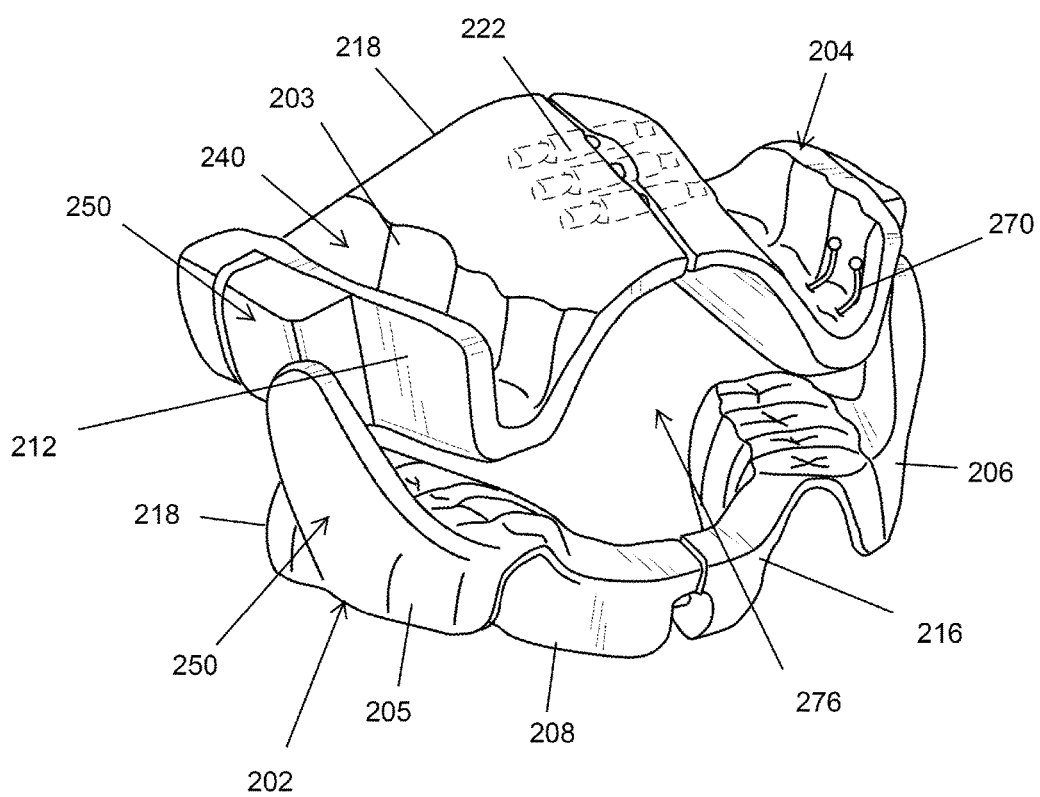
FIG. 5 is a perspective view of the upper and lower trays shown in FIGS. 1-4.

As used herein, the following terms and variations thereof have the meanings given below, unless a different meaning is clearly intended by the context in which such term is used.

"Anterior" means in the direction of or toward or adjacent the front portion of a subject's mouth and/or in the direction of or toward a source of air pressure.

"Apnea" and "sleep apnea" refer to a temporary cessation of breathing and/or to instances of shallow or infrequent breathing during sleep, generally caused by a blockage of a subject's airway (referred to as obstructive sleep apnea).

"Buccal" means in the direction of or toward a subject's cheek. In relation to a subject's teeth, this refers to the side of the teeth facing the cheek.

"Clasp" refers to a structure for securing one component or object to another.

"Coronal plane" refers to a hypothetical planar surface that extends through the body from the head to the feet, and divides the body into front and rear halves.

"Coronal surface" refers to the biting surface of a tooth. In posterior teeth this surface is generally referred to as an occlusal surface, while on anterior teeth the term incisal surface can be used.

"Downward" and "downwardly" mean in the direction of or toward a lower portion of a subject's body. "Upward" and "upwardly" mean in the opposite direction, i.e. in the direction of or toward an upper portion of a subject's body.

"Elongated" refers to a configuration or shape having a length which is longer than its width.

"Expandable," with reference to a connecting mechanism used in the present device, refers to the ability to increase in extent or range, in particular the distance between two portions of a tray of the present device.

"Facial," in the context of the present appliance, means in the direction of, toward, or adjacent to a subject's cheek and/or lips.

"Fastener" refers to a component of the present appliance that mechanically joins or affixes two or more objects together. Fasteners are used to retain elastic bands, and can take the form of a button or hook.

"Horizontal," with respect to the present appliance, refers to disposition in a plane approximately perpendicular to the sagittal and/or the coronal plane of a subject, i.e. within 15 degrees of a perpendicular plane.

"Inward" and "inwardly" refer to a direction which is toward a surface or feature of the present device.

"Labial" means in the direction of, toward, or adjacent to a subject's lips. In relation to a subject's teeth, this refers to the side of the front teeth facing the lips.

"Lateral" means away from the sagittal plane of a subject.

"Left" means to the left of the sagittal plane of a subject, from the perspective of the subject.

"Lingual" means in the direction of, toward, or adjacent to a subject's tongue. In relation to a subject's teeth, this refers to the side of the teeth facing the tongue.

"Lower" refers to the relative position of a component in the present appliance which is closer to or toward a lower portion of a subject's body when being used.

"Mandibular dentition" refers to the teeth of the lower jaw.

"Maxillary dentition" refers to the teeth of the upper jaw.

"Mechanically connected" means physically connected, either through a connection based on direct physical contact or via another mechanical structure.

"Medial" means toward the sagittal plane of a subject.

"Orthodontics" refers to the repositioning of a patient's teeth, which in some cases involves modifying the dimensions of a patient's jaw or jaws, for aesthetic or therapeutic reasons. "Orthodontic" describes an item used in orthodontics.

"Orthodontic tray" refers to a structure comprising a receptacle for receiving the upper or lower dentition of a subject. The receptacle has an opening for receiving teeth and an interior surface with sockets or depressions sized to receive a subject's teeth.

"Outward" and "outwardly" refer to a direction which is away from a surface or feature of the present device.

"Posterior" means in the direction of or toward or adjacent the rear portion of a subject's mouth and/or away from a source of air pressure.

"Right" means to the right of the sagittal plane of a subject, from the perspective of the subject.

"Sagittal" and "sagittally" refer to a direction or extent between dorsal and ventral portions of a subject or between anterior and posterior portions of a device or portion thereof.

"Sagittal plane" refers to an imaginary plane that travels vertically from the top to the bottom of the body of a subject, dividing it into left and right portions.

"Subject" refers to a user of the present appliance, usually a human user.

"Thermoplastic" refers to a material, generally a polymer material, which may be softened by heat and hardened by cooling in a reversible physical process. The thermoplastic materials used in some components of the present appliance retain their shape at 100° F. and preferably become soft (deformable) at a temperature of 212° F. or below.

"Tray," as used herein, refers to a portion of the present appliance comprising an open area for receiving the teeth of a subject, which teeth may be covered by an orthodontic tray.

"Treat" and "treatment" refer to an intervention which attenuates, prevents, or cures a physiological or medical condition of a subject.

"Upper" refers to the relative position of a component in the present appliance which is closer to or toward an upper portion of a subject's body when being used.

"Vertical," with respect to the present appliance, refers to disposition in a plane approximately parallel to the sagittal and/or the coronal plane of a subject, i.e. within 15 degrees of such a parallel plane. Preferably, vertical refers to a direction toward or away from a subject's head or feet.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Orthodontic Trays

Figure 6:
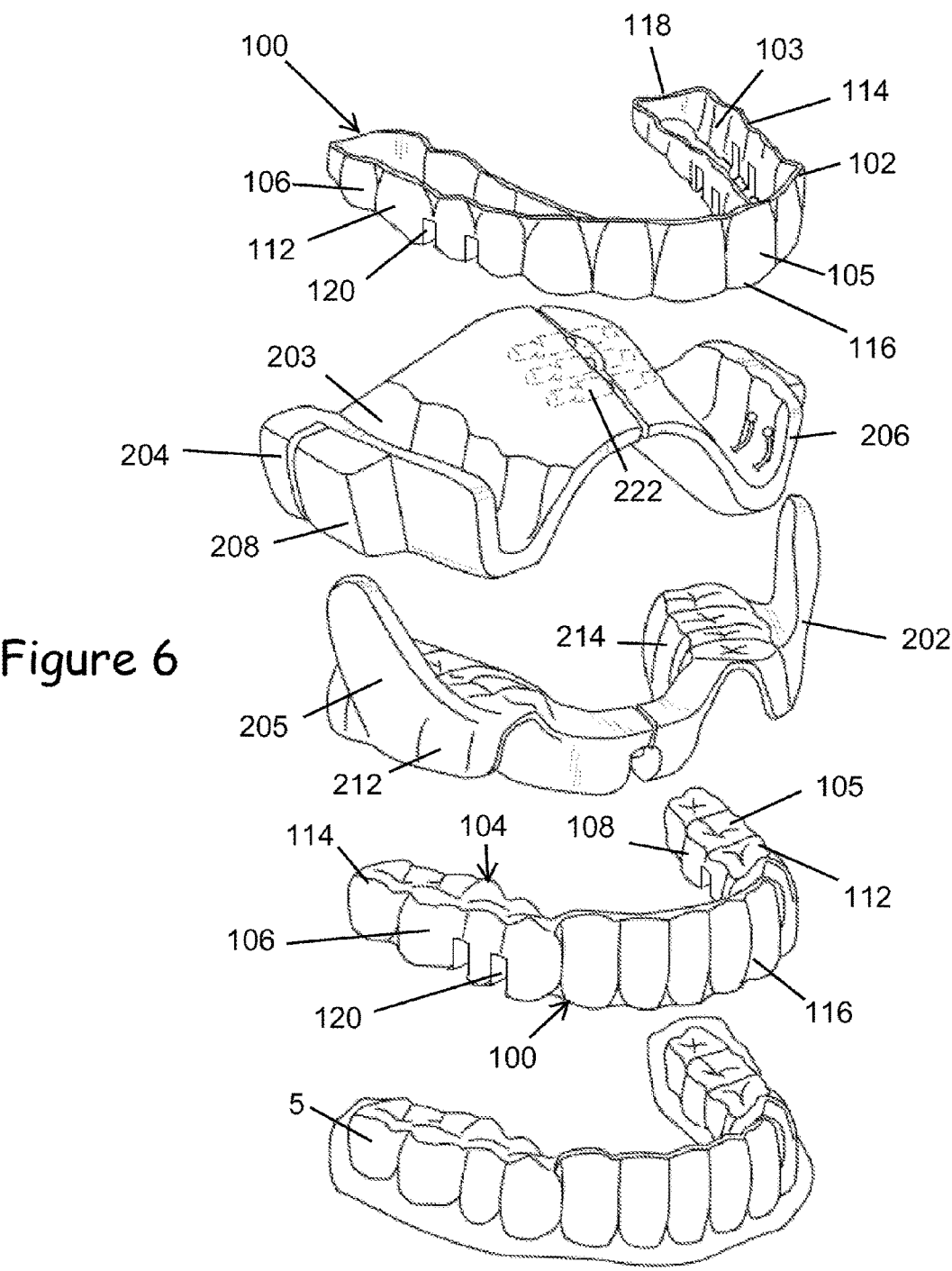
FIG. 6 is an exploded perspective view of the upper and lower trays shown in FIGS. 1-4 together with orthodontic trays.

The present sleep apnea oral appliance is designed for use in combination with orthodontic appliances that comprise a dental tray or "shell," typically formed from a polymer material. The present sleep apnea appliance is attached to such a dental tray orthodontic appliance (referred to herein as an "orthodontic tray") used by a subject, so that the subject can continue using the orthodontic tray appliance while at the same time obtaining relief from sleep apnea. As shown in FIG. 6, orthodontic trays 100 usually comprise an upper portion 102 and a lower portion 104. Each of the orthodontic trays comprise an inner surface 103 for contacting at least some of a subject's teeth 5, an outer surface 105, a buccal side 106, a lingual side 108, an anterior portion 116, a posterior portion 118, a right side 112, and a left side 114.

Individual orthodontic trays can comprise a polymeric shell having a tooth-receiving receptacle or cavity formed therein. A series of such orthodontic trays are designed and applied to a subject over time in order to reposition individual teeth in successive steps. The successive use of a number of such tray appliances permits each appliance to be configured to move individual teeth in small increments, typically less than 2 mm, preferably less than 1 mm, and more preferably less than 0.5 mm. These limits refer to the maximum linear translation of any point on a tooth as a result of using a single appliance. The interior surfaces of successive orthodontic trays in a series may thus differ in their tooth-conforming configuration by typically less than 2 mm, preferably less than 1 mm, and more preferably less than 0.5 mm.

The tooth-receiving cavity of such an orthodontic tray typically has a geometry corresponding to an intermediate or end tooth arrangement intended for that appliance. When a tray appliance is first worn by the subject, certain of the teeth will be misaligned relative to an undeformed geometry of the appliance cavity. The appliance is sufficiently resilient to accommodate or conform to the misaligned teeth, but will apply sufficient resilient force against such misaligned teeth to reposition the teeth to the intermediate or end arrangement desired for that treatment step. The appliance will preferably, but not necessarily, fit over all teeth present in the upper or lower jaw. In some cases, only certain teeth will be repositioned while others will provide a base or anchor region for holding the repositioning appliance in place as it applies the resilient repositioning force against the tooth or teeth to be repositioned.

A patient's teeth are repositioned from an initial tooth arrangement to a final tooth arrangement by placing a series of incremental position adjustment appliances in the patient's mouth. The first tray appliance of the series will have a geometry selected to reposition the teeth from the initial tooth arrangement to a first intermediate arrangement. After the first intermediate arrangement is approached or achieved, one or more additional (intermediate) appliances will be successively placed on the teeth, where such additional appliances have geometries selected to progressively reposition teeth from the first intermediate arrangement through successive intermediate arrangement(s). The treatment will be finished by placing a final appliance in the patient's mouth, where the final appliance has a geometry selected to progressively reposition teeth from the last intermediate arrangement to the final tooth arrangement.

In order to design a series of orthodontic trays that will reposition a particular subject's teeth, a digital data set representing an initial tooth arrangement and a final tooth arrangement can be determined. The initial data set representing the initial tooth arrangement, which can be presented as a visual image, is manipulated to reposition individual teeth. A final digital data set is then produced which represents the final tooth arrangement with repositioned teeth. The initial digital data set may be provided by conventional techniques, including digitizing X-ray images, images produced by computer-aided tomography (CAT scans), images produced by magnetic resonance imaging (MRI), and/or by other methods known to the art for producing three-dimensional digital representations of a subject's teeth. Alternatively, the initial digital data set may be provided by producing a plaster cast of the patient's teeth (prior to treatment) by conventional techniques, for example, and the plaster cast can then be scanned using laser or other scanning equipment to produce a high resolution digital representation of the plaster cast of the patient's teeth.

Once the initial and final data sets have been determined, a series of intermediate data sets, representing intermediate tooth positions for a subject's teeth, are determined. The successive intermediate digital data sets are preferably produced by determining positional differences between selected individual teeth in the initial data set and in the final data set and interpolating the differences. Such interpolation may be performed over at least three discrete stages, embodied in three different orthodontic trays, more often at least ten, sometimes at least twenty-five, and occasionally forty or more. The interpolation can be a linear interpolation for some or all of the positional difference, or alternatively may be nonlinear. The positional differences will correspond to tooth movements where the maximum linear movement of any point on a tooth is preferably 2 mm or less, usually 1 mm or less, and preferably 0.5 mm or less.

Once the intermediate and final data sets have been determined, the appliances can be fabricated, such as with a rapid prototyping device or digital printer. Preferably, the appliance is polymeric and is formed from a thin sheet of a suitable elastomeric polymeric, such as Tru-Tain 0.03 in. thermal forming orthodontic material (Tru-Tain Plastics, Rochester, Minn. 55902). One structure corresponding to each of the orthodontic trays is produced.

The foregoing orthodontic trays and their use in orthodontic treatment are described in U.S. Pat. No. 5,975,893 and in other patents assigned to Align Technology, Inc., including U.S. Pat. Nos. 6,210,162, 6,217,325, 6,398,548, 6,626,666, 6,629,840, 6,699,037, 7,134,874, 7,474,307, 8,105,080, and 8,562,340.

Sleep Apnea Oral Appliance

Appliance Tray

The present appliance trays are adapted to fit over orthodontic trays, in order to allow the orthodontic trays to be worn during sleep while concurrently treating a subject's snoring or apnea. Current orthodontic trays (described above) and apnea appliance designs do not allow such concurrent wear. In order to allow this, the present appliance trays and orthodontic trays are designed to cooperate, as described further below.

The appliance tray 200 generally comprises a lower portion 202, an upper portion 204, an inner surface 203, an outer surface 205, a right side 206, a left side 208, a buccal side 212, a lingual side 214, an anterior portion 216, and a posterior portion 218. As seen in FIG. 6, the lower portion 202 and upper portion 204 comprise receptacles 240 which are configured to fit around the outer surface 104 of the orthodontic trays 102 and 104 respectively, such that an interior surface of the lower portion 202 of the present sleep apnea appliance 200 surrounds at least a portion of the outer surface 105 of the lower portion 102 of the orthodontic tray and contacts at least a portion of the exterior surface 105. The interior surface of the upper portion 204 of the sleep apnea appliance 200 likewise surrounds and contacts at least a portion of the outer surface 105 of the upper portion 104 of the orthodontic tray.

Preferably, the inner surface of each of the appliance trays 200 conforms to the outer surface 105 of the corresponding orthodontic tray 100. In a particularly preferred embodiment, the inner surface 203 of the receptacles 240 of each appliance tray 200 is configured to fit the exterior (outer) surfaces 104 of all of the orthodontic trays 100 when a series of orthodontic trays 100 is used. The outer surface of each orthodontic tray 100 in the series may comprise a different configuration, so in order to be able to fit all of the planned configurations, an initial data set representing the configuration of the outer surface of a respective orthodontic tray 100 for an initial tooth arrangement is determined. A final data set representing the configuration of the outer surface of a respective orthodontic tray 100 for a final tooth arrangement is also determined. These data sets are combined so as to determine a configuration for the respective appliance tray 200 allowing both the initial and final configuration of the orthodontic tray 100 to be accommodated.

Each of the orthodontic trays 100 is generally fitted onto all of a subject's maxillary dentition or mandibular dentition, as the case may be, though this is not mandatory. The present appliance trays 200 preferably extend only over the rear dentition, i.e. not over the incisors and preferably not over the canine teeth, which are often the teeth most subject to being repositioned by orthodontic treatment. In addition, by forming the receptacles 240 over only the rear dentition, an anterior opening 276 for air flow is provided when the oral appliance is worn by the subject. Since the intermediate tooth positions formed by orthodontic trays 100 are likely to change more for the incisor and canine teeth, the configuration of the sleep apnea appliance 200 shown in the illustrated figures may also allow the present appliance 200 to be use with a greater number of orthodontic trays 100.

The appliance trays can be formed from a variety of orally compatible materials, typically polymers. In one embodiment, acrylic is used to form the present appliance. Thermoplastic polymers, thermosets, thermoplastic elastomers, and other materials can also be used. The thermoplastic materials that are used must be capable of retaining their shape when used by a subject, and thus must remain solid at about 100° F., and preferably remain solid at somewhat higher temperatures, such as at 110° F., 120° F., or higher. When thermoplastic materials are used to form the present trays, they preferably become deformable at a temperature of 212° F. or less, so that they can be made plastic by being placed in boiling water. Preferably, the material is not deformable at less than 120° F., preferably at not less than 145° F.

Clasps

The clasps 270 used in the present device can be configured in any of a number of ways known to those of skill in the art. Representative clasp designs used in oral and orthodontic devices include Adam's clasps (double clasps), ball clasps, C clasps (three-quarter clasps), Jackson's clasps (full clasps), Southend clasps, Duyzing clasps, Schwarz clasps, and Eyelet clasps. Clasps are formed from a rigid material which can be bent, deformed, or otherwise shaped to a desired configuration while maintaining sufficient rigidity to contact and grip a surface, in particular a tooth surface of a subject. Preferred materials include metals, such as stainless steel or other appropriate material. The ability to bend the clasp material allows fitting of the appliance tray on a subject's dentition to be adjusted as the subject's teeth and/or jaws are repositioned through orthodonture.

Clasps 270 are typically formed from metal wire, which can be bent to a desired shape. Such metal wire can be formed as a loop, with both ends embedded in or otherwise secured to a portion of the present device, or can be formed with only one end secured to the device. A preferred clasp is a ball clasp, as shown in the illustrated embodiments. A ball clasp is typically formed from a wire in which a proximal end 272 is secured to a respective appliance tray 200 while a distal end 274 extends outwardly from an inner surface of an appliance tray. A ball clasp comprises a "ball," typically a spherical shape, for contacting a subject's tooth surface (though other shapes are possible). The clasps 270 are preferably positioned to exert force between two teeth, preferably at the interproximal contact point between the teeth. In order to better retain an orthodontic tray 100, the orthodontic tray 100 can be provided with spaces to allow the clasp 270 to contact the teeth of a subject, and/or can be provided with a groove to fit the contour of the clasp 270.

In order for the clasps 270 to be able to contact a subject's tooth surface, the orthodontic trays are provided with openings 120 which extend from their outer surfaces 105 to their inner surfaces. The openings 120 are positioned so that when the present appliance tray 200 is worn over a respective orthodontic tray 100, the clasps 270 of the appliance tray 200 extend through the openings 120 to the subject's tooth surface, thereby securing both the appliance tray 200 and the orthodontic tray 200 to the subject's teeth and jaw.

Lateral Connectors

In general, if the amount of arch development in a subject is 4 millimeters or less, i.e. if the distance between the midpoints of corresponding premolars or molars on each lateral side of a patient's maxillary and/or mandibular dentition increases by 4 millimeters or less, then a single sleep apnea appliance 200 can be used with the various orthodontic tray appliances 100 used to alter a subject's dentition. In order to accommodate the expansion of a subject's dentition, however, the present appliance trays 200 are preferably formed from separate left side portions 206 and right side portions 208 which are joined respectively by one or more expandable lateral connectors 222 in a center portion of each sleep apnea device portion 201. As the subject's arch is expanded, the connectors 222 can be actuated to further separate each of the respective left side portions 206 from the right side portions 208. For example, actuating the connector 222 in the upper tray 202 can increase the lateral distance between a left lateral end and a right lateral end of the upper tray 202.

The expandable connectors, used for example for the lateral connectors 222, preferably comprise a threaded connection, such as a screw in threaded engagement with a fitting, in order to allow the lateral distance between the right side portion and the left side portion of the appliance trays to be adjusted by rotating the fitting relative to the screw. The expandable connectors are typically expansion screws, which comprise at least a threaded spindle having a hole or other engagement mechanism in a central portion and threadably engaged blocks on either side of the hole.

Figure 7:
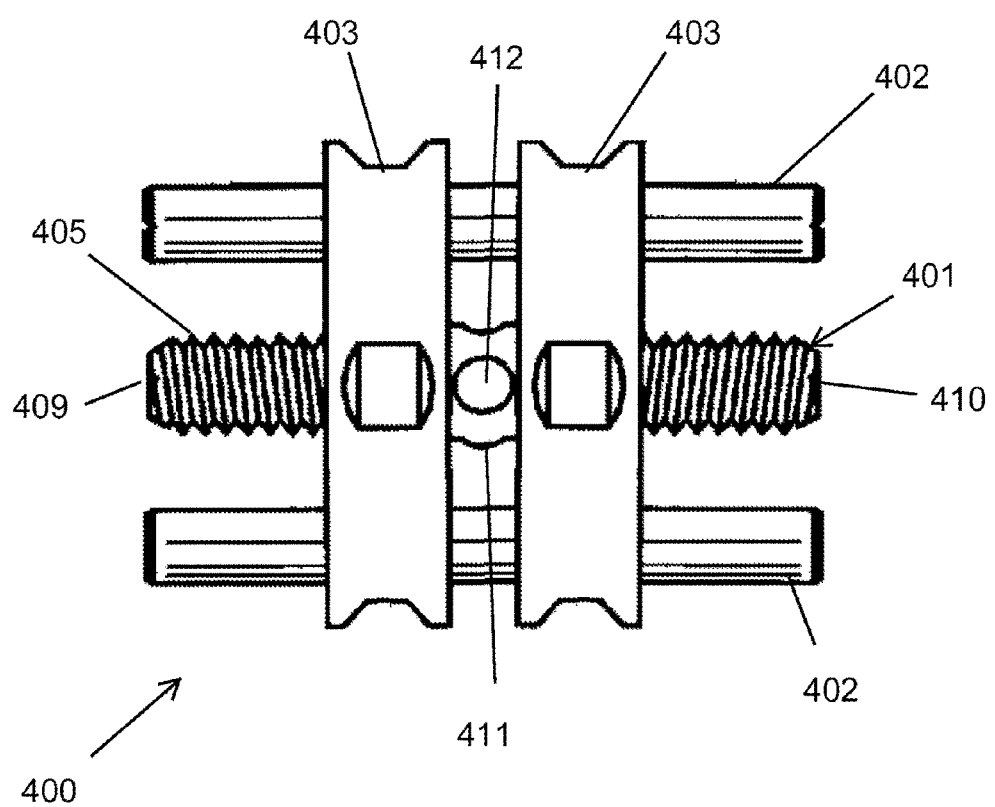
FIG. 7 is a side elevation view of an orthodontic expansion screw.
Figure 8:
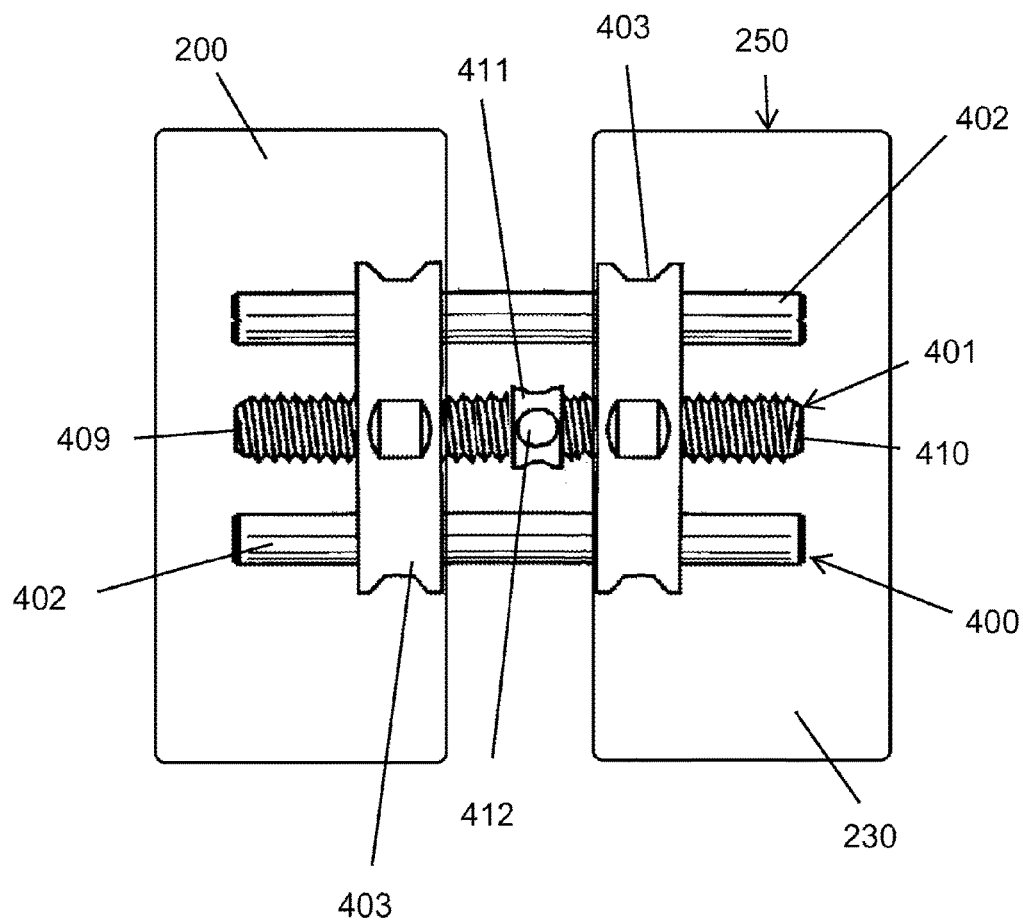
FIG. 8 is a side elevation view of the orthodontic expansion screw of FIG. 8 embedded in an appliance.

An example of an orthodontic expansion screw is shown in FIGS. 7 and 8. An expansion screws typically comprises a spindle 401 with counter-rotating threads 405 on its two sides 409, 410 and with a central enlargement 411 having a plurality of recesses or holes 412 to be individually engaged, by means of an actuating pin rod-like tool to drive spindle 401 into rotation about its longitudinal axis. Associated with the spindle 401 are two cylindrical and parallel rods 402. These rods extend through peripheral holes of two blocks 403 located on opposite sides with respect to the enlargement 411 of spindle 401, thereby forming a slide guide for the movement of two portions of the present device 1. When the central enlargement 411 is turned, the blocks 403 are moved toward or away from each other, depending on the direction of rotation of the central enlargement 411.

As illustrated FIG. 8, each of the blocks 403 is secured to a respective component of the present device 10, such as the right side portion or left side portion of an appliance tray 10 of the present device 1, preferably by embedding the block 403 and adjacent portions of the spindle 401 and rods 402 in a polymer plastic material. The central enlargement 411, however, is not embedded and/or encased in plastic, in order to allow it to be accessed.

Other mechanisms which allow adjustment of the distance between respective components of the present device can also be used as adjustable connectors. For example, geared or ratcheting mechanisms can be employed.

Anchors

In order to maintain the upper tray 204 and lower tray 202 in a desired relative position, at least one projection is provided in each of the left side portions 206 and right side portions 208 of the upper tray 204 and lower tray 202. These projections 250 extend laterally from the buccal side of the right side portion and the left side portion and form anchors for mechanically connecting the left side portion of a first appliance tray to the left side portion of a second appliance tray. These anchors can be in the form of a button, a hook 450 (as seen for example in FIG. 9), or a Herbst screw, which are connected using appropriate connectors such as orthodontic rubber bands, telescoping shims, and/or plastic connectors.

In the embodiment illustrated in FIGS. 1-6, each lateral side of the lower portion 202 is provided with a laterally extending projection 230, and each lateral side of the upper portion 204 is likewise provided with a laterally extending projection 230. In the illustrated embodiments, laterally extending projection 230 of the lower portion 202 has a rearward-facing surface which is designed to contact a forward facing surface of the laterally extending projection 230 of the upper portion 204. For example, rearward-facing surface 232 on the right side of lower portion 202 is designed to contact forward facing surface 234 on the right side of the upper portion 204. Other configurations of the laterally extending portions 230 are also possible. The position of the mandible can be adjusted forward or rearward as needed using adjustment screws 240, which can be the same types of mechanisms used for the lateral connectors described above.

Method of Use

In order to treat either snoring or sleep apnea, the present appliance 200 is provided with opposing surfaces on the upper portion 204 and lower portion 202. The opposing surfaces are in contact when the appliance 200 is being worn by a subject, and the anchors described above serve to maintain the mandible in a relatively forward position during sleep.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A method for accomplishing an orthodontic treatment while treating snoring and/or sleep apnea in a subject, comprising:
  applying a first orthodontic tray to maxillary dentition of a subject, wherein the first orthodontic tray has an anterior portion, a posterior portion, a right side, a left side, an inner surface, and an outer surface, wherein the inner surface of the first orthodontic tray contacts at least some of the subject's maxillary dentition;
  applying a second orthodontic tray to mandibular dentition of the subject, wherein the second orthodontic tray has an anterior portion, a posterior portion, a right side, a left side, an inner surface, and an outer surface, wherein the inner surface of the second orthodontic tray contacts at least some of the subject's mandibular dentition;

applying a first appliance tray over the first orthodontic tray, the first appliance tray having an anterior portion, a posterior portion, a right side, a left side, a buccal side, a lingual side, an inner surface, and an outer surface, wherein a receptacle formed in the inner surface of the first appliance tray contacts and surrounds at least a portion of the outer surface of the first orthodontic appliance; and applying a second appliance tray over the second orthodontic tray, the second appliance tray having an anterior portion, a posterior portion, a right side, a left side, a buccal side, a lingual side, an inner surface, and an outer surface, wherein a receptacle formed in the inner surface of the second appliance tray contacts and surrounds at least a portion of the outer surface of the second orthodontic appliance, wherein the first appliance tray and second appliance tray cooperate to maintain the mandible of the subject in a relatively forward position during use, thereby treating snoring and/or sleep apnea in the subject.

2. The method of claim 1, wherein the first orthodontic tray is fitted onto all of the subject's maxillary dentition.

3. The method of claim 1, wherein the second orthodontic tray is fitted onto all of the subject's mandibular dentition.

4. The method of claim 1, wherein the orthodontic trays comprise a series of first orthodontic trays and a series of second orthodontic trays, and wherein each of the orthodontic trays in each series comprises a different configuration in order to change the position of the subject's teeth and/or the shape of the subject's jaw.

5. The method of claim 1, wherein the first orthodontic tray comprises one or more openings between the outer surface and the inner surface and the first appliance tray comprises clasps, the clasps corresponding to and fitting within the one or more openings of the first orthodontic tray when the first orthodontic tray and first appliance tray are worn by the subject.

6. The method of claim 5, wherein the clasps are selected from the group consisting of Adam's clasps (double clasps), ball clasps, C clasps (three-quarter clasps), Jackson's clasps (full clasps), Southend clasps, Duyzing clasps, Schwarz clasps, and Eyelet clasps.

7. The method of claim 1, wherein the second orthodontic tray comprises one or more openings between the outer surface and the inner surface and the second appliance tray comprises clasps, the clasps corresponding to and fitting within the one or more openings of the second orthodontic tray when the second orthodontic tray and second appliance tray are worn by the subject.

8. The method of claim 7, wherein the clasps are selected from the group consisting of Adam's clasps (double clasps), ball clasps, C clasps (three-quarter clasps), Jackson's clasps (full clasps), Southend clasps, Duyzing clasps, Schwarz clasps, and Eyelet clasps.

9. The method of claim 1, wherein the first appliance tray comprises a first expandable lateral connector for mechanically connecting a left side portion and a right side portion of the first appliance tray, wherein the expandable lateral connector can be adjusted to lengthen the lateral distance between the right side portion and the left side portion of the first appliance tray.

10. The method of claim 9, wherein the expandable lateral connector is an expansion screws.

11. The method of claim 9, wherein the second appliance tray comprises a second expandable lateral connector for mechanically connecting a left side portion and a right side portion of the second appliance tray, wherein the second expandable lateral connector can be adjusted to lengthen the lateral distance between the right side portion and the left side portion of the second appliance tray.

12. The method of claim 11, wherein the second expandable lateral connector is an expansion screws.

\* \* \* \* \*